United States Patent [19]

Verbiscar

[11] Patent Number: 5,268,467
[45] Date of Patent: Dec. 7, 1993

[54] IMMUNOMODULATORY POLYSACCHARIDE FRACTIONS FROM ASTRAGALUS PLANTS

[76] Inventor: Anthony J. Verbiscar, 491 Crestvale Dr., Sierra Madre, Calif. 91024

[21] Appl. No.: 490,364

[22] Filed: Mar. 8, 1990

Related U.S. Application Data

[63] Continuation-in-part of Ser. No. 197,631, May 23, 1988, abandoned.

[51] Int. Cl.$^5$ .............. C08B 37/00; C07H 1/00; C07H 3/00
[52] U.S. Cl. ................. 536/123; 536/123.1; 536/124
[58] Field of Search ............. 536/114, 127, 128, 123, 536/123.1; 514/885, 783, 54

[56] References Cited

U.S. PATENT DOCUMENTS

| | | | |
|---|---|---|---|
| 2,666,759 | 1/1954 | Wood. | |
| 3,226,378 | 12/1965 | Wilson. | |
| 4,511,559 | 4/1985 | Szendrei et al. | 514/54 |
| 4,843,067 | 6/1989 | Liu | 514/54 |

OTHER PUBLICATIONS

Sun et al. Cancer 52: 70–73 (1983).
Sun et al. J. Biol. Response Modifiers 2: 227–237, 1983.
Yunde et al. Chinese Medical Journal 94(1): 35–40, 1981.
Chemical Abstracts 1982, 96: 177941r, Fang et al.
Youji Huaxue 1: 26–31, 1982.
He et al. J. of Natural Products 54(3): 810–815, 1991.
Gentry, H. S. Economic Botany 11: 40–63, 1957.
Anderson, D. M. W. Food Additives and Contaminants 6(1): 1–12, 1989.
Anderson et al. Phytochemistry 24(10): 2301–2304, 1985.
Anderson et al. Food Hydrocolloids 3(3): 217–223, 1989.
Weber et al. Pharmacology 17: 39–49, 1978.
Carr et al. J. of the Royal Microscopical Society 88(2): 205–210, 1968.
Galbraith et al. British J. of Cancer 17: 738–744, 1963.
Generally Recognized as Safe Food Ingredients: Gum Tragacanth, Informatics, Inc. NTIS U.S. Dept. Commerce, Jul. 1972.
Mayhew et al. British J. Cancer 18: 537–542, 1964.
Nakahara et al. Gann 55: 283–288, 1964.
Domenjoz et al. 18: 1495–1498, 1968.
Roe, E. M. F. Nature 184: 1891–1892, 1959.
Roe et al. Cancer Research 32: 2067–2074, 1972.
Seljelid et al. Exp. Cell Res. 131: 121–129, 1981.
Strobel et al. Toxicology Letters 14: 247–252, 1982.
Belkin et al. Cancer Research 19: 1050–1062, 1959.

*Primary Examiner*—Johnnie R. Brown
*Assistant Examiner*—Gary L. Kunz

[57] ABSTRACT

Polysaccharides from the gum exudates of Astragalus species Tragacantha section plants are extracted and modified into water-soluble fractions free from small molecular impurities. Such polysaccharide fractions upon parenteral administration inhibit specific tumors and viruses in mammals away from the site of injection, presumably by immunostimulatory effects. These polysaccharide fractions show no toxicity upon parenteral administration.

9 Claims, 2 Drawing Sheets

IMMUNOMODULATORY POLYSACCHARIDE FRACTIONS FROM ASTRAGALUS PLANTS

This is a continuation-in-part of Ser. No. 07/197,631 filed May 23, 1988, now abandoned.

FIELD OF THE INVENTION

This invention concerns the preparation and use of purified fractions of a polysaccharide exudate of certain Astragalus plant species, which inhibit cancers and viruses in mammals and can be used to treat immunological related disorders. More particularly, it relates to aqueous infusions of polysaccharides from certain Tragacantha section Astragalus species which have immunomodulatory activity to inhibit the formation, growth, multiplication and spread of malignant tumors, to inhibit the replication of pathogenic viruses, and to treat other immunologically susceptible diseases.

BACKGROUND OF INVENTION

The genus Astragalus, family Leguminosae, comprises 2000 or more species widely distributed throughout the world, of which only certain plants, in the section Tragacantha, produce a polysaccharide rich exudate. Most of the polysaccharide gum producing species are indigenous to the Middle East countries from Eastern Turkey, Azerbaijan, Syria, Iraq and Iran to Western China. The gum from these Astragalus species is a commercial commodity called tragacanth. It is used in foods as a stabilizer, thickener and emulsifier, and in pharmaceutical products as a suspending agent. It is generally recognized as safe (GRAS) under Food and Drug Administration classification for use in foods in the United States. Other countries also classify tragacanth as safe for food additive use.

The gum is stored in the central cylinder of the tap root of the plant. It is collected from the live plant by cutting a slot or drilling a hole in the root cylinder below the crown, whereupon the gum exudes out as a ribbon. The gum dries within 1-2 hours becoming semi-brittle, and can be picked off by hand. The gum contains both water-soluble and insoluble polysaccharides and other minor components. The chemically heterogeneous whole dried exudates are marketed as tragacanth ribbon or powder. In the past it was estimated that as much as one million pounds of tragacanth per year were harvested from wild plants for food additive and pharmaceutical uses.

Roe (1959) found that some tragacanth powders inhibited the multiplication of cancer cells in the peritoneal cavity of mice. Suspended Landschutz ascites cancer cells were implanted in the peritoneal cavity of mice where they multiplied and could be assayed by counting techniques. The serous fluid of the peritoneal cavity was an ideal medium for the reproduction and growth of these transplanted ascites cancer cells. The ascites cancer cells were cultured in the peritoneal cavity and multiplied under normal conditions. When commercial tragacanth in water was injected into the peritoneal cavity the multiplication of cancer cells was inhibited. Roe assumed that the tragacanth had a direct cytostatic action on the cancer cells. The inhibition was explained by an association of the polysaccharide with the ascites cancer cell wall, with resultant inhibition of mitosis. This phenomena was examined in a series of Roe et al. articles following the initial report (Galbraith et al., 1962, 1963; Mayhew and Roe, 1964a, 1964b, 1965; Carr and Roe, 1967, Roe et al., 1972). In addition to the Landschutz strain, Roe worked with Crocker, Bp8 and C+ leukemia ascites cancer cells in the peritoneal cavity. She investigated tragacanth powders from what she believed was *Astragalus gummifer* a commonly used but inaccurate designation for Astragalus species producing the gum, and a type "tragacanth" from Indian *Sterculia urens*, which was actually karaya gum. These were the only two plant species mentioned by Roe in her studies of tragacanth.

Roe et al. (1972) reported their final study on the interaction of tragacanth with ascites cancer cells both in vivo and in vitro. In this study with commercial tragacanth, the mitosis inhibitory component was found to be located exclusively in the water-soluble fraction. As in the earlier work from this laboratory, the degree of inhibition of water-soluble fractions was assayed by counting the ascites cancer cells taken from the peritoneal cavity of an infected mouse. The inhibitory activity of the water-soluble fraction was destroyed by boiling for five minutes. In none of the Roe et al. reports were the studies ever extended to cancers that occur outside of the peritoneal cavity. Direct surface contact of ascites cancer cells with intraperitoneal administered tragacanth preparations was always postulated as the governing mechanism inhibiting mitosis. Effects on cell membrane rather than immunomodulatory activity were reported to be the cause of inhibition. These surface effects of the polysaccharide affecting the cancer cell directly in the peritoneal cavity may well have been the primary cause of mitosis inhibition in the Roe group studies. The Roe studies did not consider possible immunomodulatory activity that would lead to cancer inhibition of solid tumors outside of the peritoneal cavity.

Nakahara et al. (1964) studied the effects of several plant polysaccharides on the inhibition of a cancer implanted in the groin of mice. In this investigation Ehrlich ascites cancer cells were extracted from the peritoneal cavity of one mouse and injected subcutaneously into the groin of other mice where they grew into a solid tumor. After the tumor-bearing mice were administered polysaccharides intraperitoneally, growth of the solid tumor in the groin was monitored by sacrificing the mouse with observation and weighing of the tumor mass. Bamboo polysaccharide had an inhibitory effect on the growth of the tumor in the groin, but tragacanth did not. This study demonstrated that tragacanth when administered intraperitoneally did not act on a solid tumor outside of the peritoneal cavity.

Osswald (1968) repeated the experiments of Roe using Ehrlich ascites cells propagated in the peritoneal cavity of mice. Commercial tragacanth suspended in an aqueous glucose medium was injected into the peritoneal cavity of mice 6 and 24 hours prior to intraperitoneal injection of the ascites cancer cells. After seventeen days only 5 of 15 mice on the 6 hour pretreatment regimen developed new cancer cells, whereas 12 of 15 mice on the 24 hour pretreatment regimen developed new ascites cancer cells. Three of the thirty mice in the tragacanth treatment groups actually developed solid tumors in the stomach walls in addition to the ascites cancer cells in the peritoneal cavity. Administration of polysaccharides at high doses prior to intraperitoneal injection of ascites cancer cells as in this study is not an effective way to inhibit multiplication of the cells, and appears to partially inhibit the immune system facilitating metastasis.

In summary, Roe et al (1959-1972) and Osswald (1968), were only able to inhibit multiplication of ascites cancer cells transplanted into the peritoneal cavity of mice with their tragacanth preparations injected into the same site. Osswald confirmed Roe's finding about ascites cancer cell mitosis inhibition but found that tragacanth seemed to increase the spread of the cancer to the stomach wall tissue in some of the mice. Nakahara et al. (1964) was not able to inhibit the growth of a solid groin tumor in mice with intraperitoneal administration of tragacanth. These prior studies do not predict or anticipate the antiviral and anticancer results reported herein, which are based on an immunomodulatory mechanism of action rather than a direct effect of the polysaccharide on the antigenic cancer cell or virus.

Until this invention no autochthonous solid tumors have been inhibited by tragacanth preparations. Only transplanted serous fluid ascites cancer cells growing in the peritoneal cavity have been inhibited from multiplying. In further contrast to prior art, the purified polysaccharides of tragacanth reported here, although injected intraperitoneally, act on solid tumors outside of the peritoneal cavity. In the light of prior results there was no real basis to expect any tumors outside of the peritoneal cavity to be inhibited following intraperitoneal administration of tragacanth polysaccharide fractions, much less both chemical-induced and virus-induced tumors. There were also no examples in prior art which demonstrated immunomodulatory antiviral effects for these tragacanth polysaccharides.

Furthermore, the chemical-induced and virus-induced tumors of the mammary gland and spleen reported in this disclosure are not transplanted tumors that had a separate existance outside of the host animal. There were no cancer cells initiating the tumors in these test systems as there were in the prior ascites cancer cell reports. The chemical-induced and virus-induced solid tumors are considerably different from the transplanted serous fluid ascites tumors in this regard. The chemical-induced and virus-induced solid tumors are also different from one another, one establishing selectively in the mammary gland, and the other in the spleen of rodents. An extension of immunomodulatory activity against viruses further demonstrates in this disclosure that the polysaccharides modulate the immune system, and respond to various types of antigen challenges in a non-specific manner. In this regard, Seljelid et al. (1981) reported that gum tragacanth stimulates mouse macrophage in vitro. In the latter report it was claimed that the water-insoluble polysaccharide fractions stimulated macrophage, although not all insoluble polysaccharides. This is in contrast to our conclusion that water-soluble polysaccharides stimulate macrophage in the peritoneum, a rich source of these mononuclear phagocytes. Macrophage stimulation in the peritoneal cavity is an important mechanism leading to anticancer and antivirus effects away from this site of administration of these immunomodulatory plant polysaccharides.

The prior studies of Roe (1959-1972), Nakahara (1964) and Osswald (1968) were carried out principally with aqueous commercial tragacanth suspensions which included water-soluble, insoluble and gel fractions. Roe found that inhibitory activity varied in tragacanth from different areas but did not relate this to interspecies or intraspecies differences. The differences could have been due to processing or cultural conditions. In contrast, the differences in activity of five distinct Astragalus species are disclosed here. This is the first time that any antiviral and cancer inhibitory activity has been related to different Astragalus species. Each one of the Astragalus species, Tragacantha section, plants are different in appearance and growth habit from one another. Studies demonstrate that the tragacanth polysaccharides from each species are also different. The polysaccharides from three Astragalus species of Turkish origin (Anderson and Bridgeman, 1985) and four of Iranian origin, but U.S. grown (Anderson and Grant, 1989) were shown to differ in their contents of monosaccharides including galacturonic acid, galactose, arabinose, xylose, fucose and rhamnose. The polysaccharides also differ between species in their percent nitrogen, methoxyl and ash (metal) values, as well as amino acid composition of the minor amount of protein present. Differences in the amounts of water soluble and insoluble polysaccharides were also noted. Our studies found that acidity and viscosity of water-soluble tragacanth solutions, infrared spectra and size exclusion chromatography curves were also different among the species. Because of these differences in the gum exudates from various Astragalus species, it is not surprising to find differences in antiviral and tumor inhibitory activity among species. Each plant species varies in appearance, polysaccharide chemistry, and degree of biological activity from every other species within this Astragalus genus. All of the whole gums are named tragacanth and are thereby classified in the Tragacantha section but there are physical, compositional and immunomodulatory differences in polysaccharides among the species.

Anticarcinogenesis agents that prevent formation of tumors, lower multiplicity of tumors or size in original tissues, and prevent or inhibit the spread of the tumor to other tissues, can be useful medical tools. Such agents can be used as adjuncts to surgical, drug and radiation therapies, inhibiting metastasis. Many viral diseases will be susceptible to these polysaccharide immunomodulatory agents. The tragacanth products can also be used in the treatment of patients with immunological deficient systems. Tragacanth gum has been used in foods such as ice cream, sauces and dressings for many years as a generally recognized as safe (GRAS) food ingredient (Informatics, 1972). Gum tragacanth is non-teratogenic, non-mutagenic and generally non-toxic (Anderson, 1989). However, Bachman et al. (1978) found that commercial gum tragacanth administered to rats inhibited oxidative phosphorylation in liver and heart mitochondria, and mixed function oxidases in liver. It was speculated that the small molecular impurities in gum tragacanth could have caused these negative effects. The discoveries reported here extend the prior art into new, novel and safe plant polysaccharides for the treatment of diseases and disorders susceptible to immunomodulatory agents.

SUMMARY OF INVENTION

This invention pertains to purified polysaccharide fractions from tragacanth gum which modulate the immune system. The immune system of the host is stimulated or suppressed by such fractions to combat cancer cells, virus infections or immunological disorders by natural means. Isolation and purification processes are reported which provide immunomodulatory water-soluble polysaccharide fractions free from the small molecular impurities in the crude gum which can cause negative side effects.

When administered to mammals the purified tragacanth fractions prevent the formation, multiplicity, growth and spread of autochthonous malignant tumors. The tumors can be induced by carcinogens such as N-methyl-N-nitrosourea (MNU), and by viral agents such as the amphotropic murine leukemia virus (MuLV-10A1). As examples of this anticancer activity the multiplicity of a mammary carcinoma in female rats and growth of a splenic lymphoma in mice are inhibited by water-soluble polysaccharide fractions of tragacanth reported herein. The inhibition of a lethal Punta toro virus in mice is also an example of immunomodulatory activity of these polysaccharides.

Tragacanth is composed of polysaccharides containing D-galacturonic acid, D-galactose, L-fucose, D-xylose, L-arabinose and L-rhamnose. The galacturonic acid is found principally in the polymer backbone structure, with the other five monosaccharides also in the side chains. Some of the polysaccharides are water soluble and others are insoluble. The whole gum exudate contains little or no free monosaccharides, but does contain some alcohol soluble glycosides and other metabolites detectable with thin layer chromatography (TLC) and high performance liquid chromatography (HPLC). From the TLC and HPLC data on the alcohol extracts, it is estimated that 15-20 different small molecular compounds occur in the exudates from five Astragalus species described herein. The total amount of these alcohol solubles in each species is in the range of 5% or less, Table A. The exudate also contains metal cations including potassium, calcium and magnesium, and a small amount of protein. The immunomodulatory activity of some polysaccharides has been associated with conformational factors and side chain monosaccharide sequences. The loss of activity of tragacanth in boiling water could be due to conformational changes or to hydrolysis of the side chain oligosaccharides. For this reason, all processing of tragacanth was carried out at room temperature or below. The lower temperatures used in processing maintain the integrity of the polysaccharide toward chemical and conformational changes that may occur, and thereby maintain immunomodulatory activity.

A BRIEF DESCRIPTION OF THE DRAWINGS

FIG. 1 presents the infrared spectra of tragacanth polysaccharide water-soluble fraction AV213-A and of the tragacanth polysaccharide water-soluble fraction AV213-B after treatment with a cation exchange resin in hydrogen form.

Figure 1:
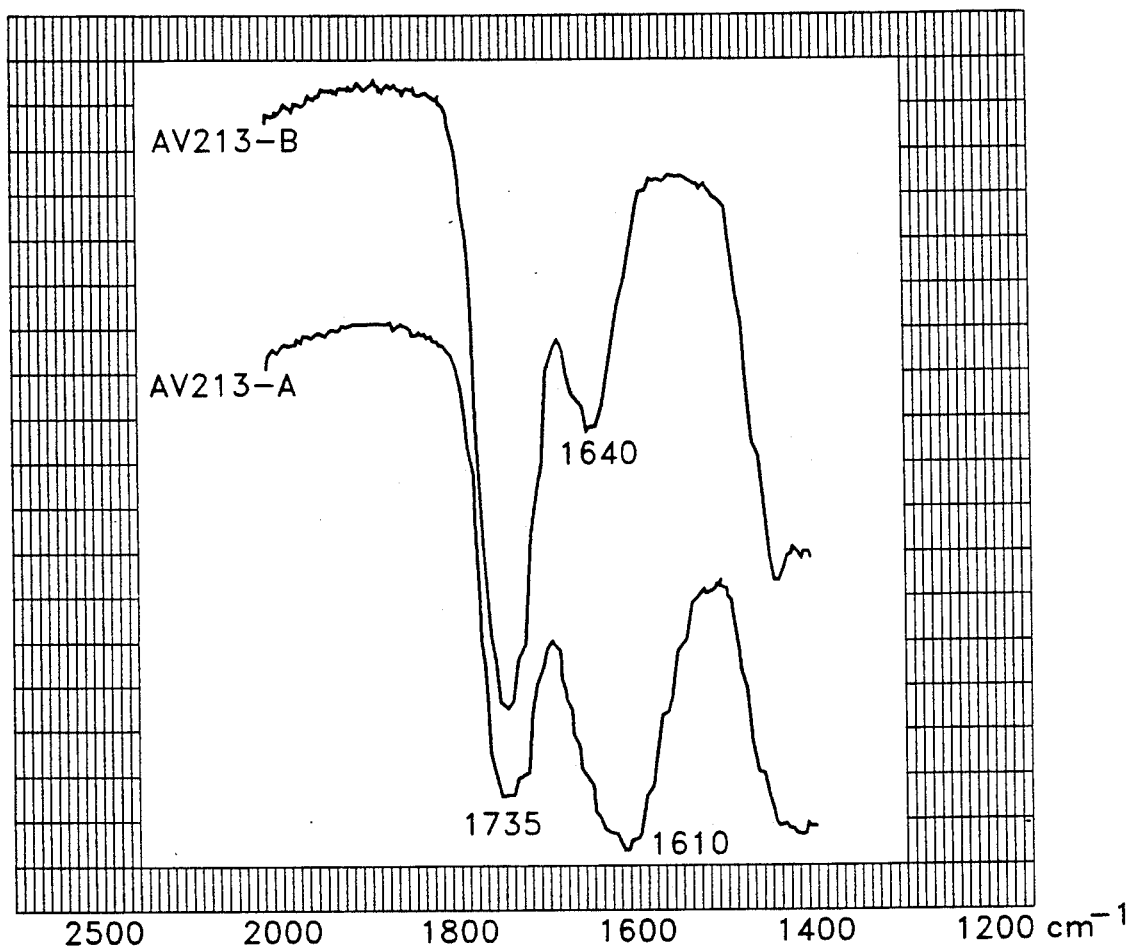
Figure 2:
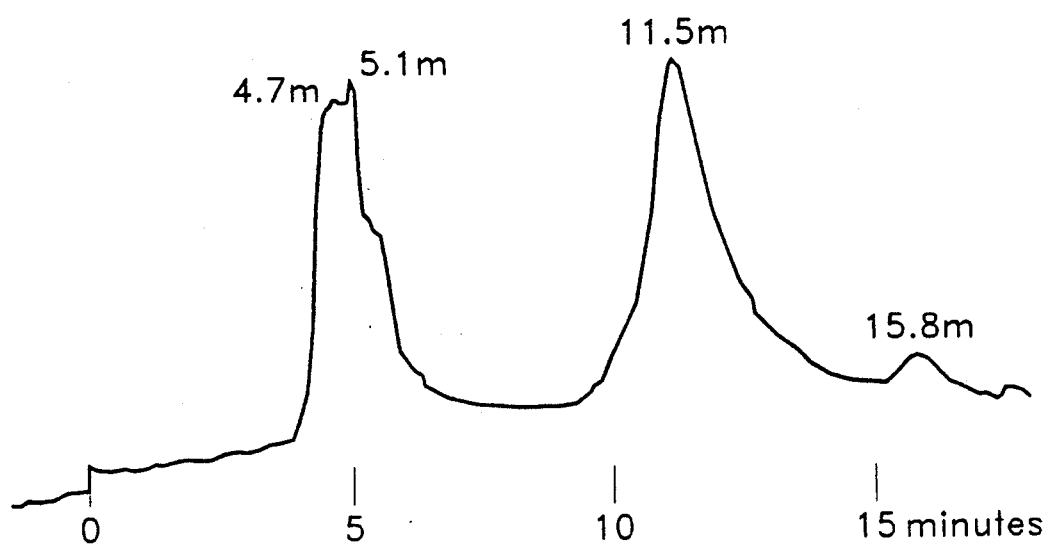
FIG. 2 is the size exclusion chromatograph of tragacanth polysaccharide initial water-soluble fraction AV213-C measured at 210-220 nm.
Figure 3:
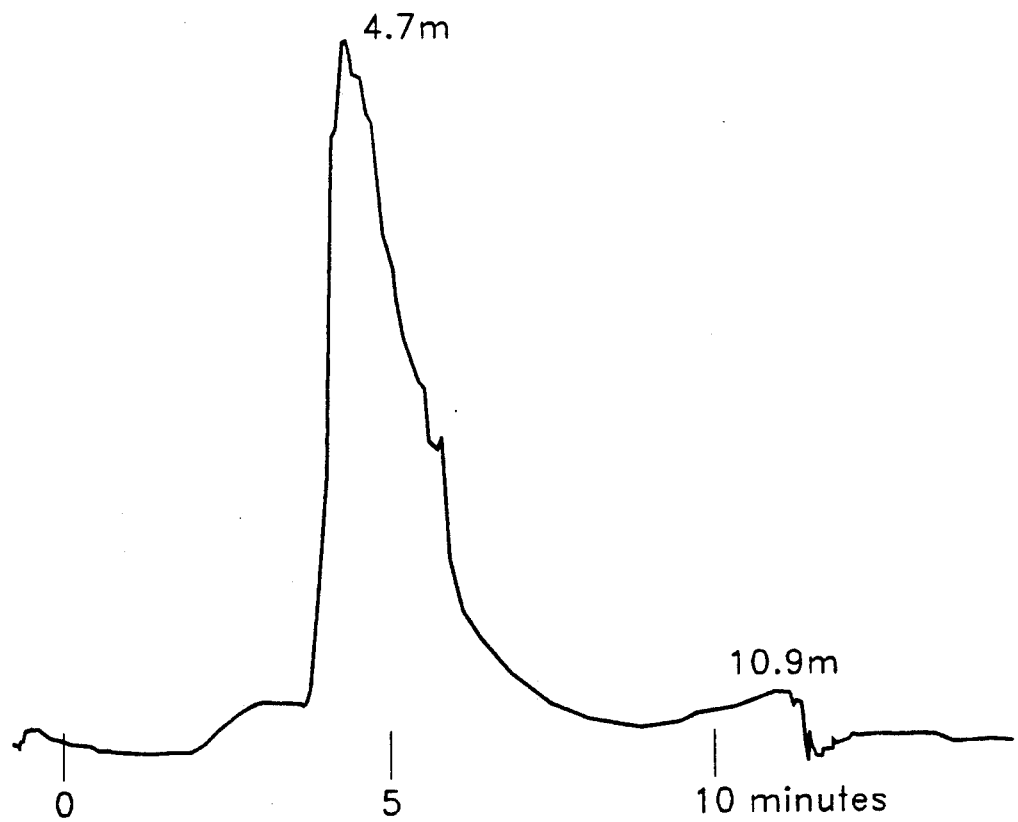
FIG. 3 is the size exclusion chromatograph of tragacanth polysaccharide after extraction with alcohol (AV213-D) measured at 210-220 nm.

Tragacanth gum exudates were fractionated into water-soluble, water-insoluble and alcohol-soluble parts. Extraction and ion exchange processes were used. Tragacanth ribbon from multiple plants of each species were collected, combined and stored under refrigeration until ready for processing. A sample of tragacanth powder obtained from a commercial source termed Astragalus spp. #1 was also separated into three fractions. Total recovery in the three fractions varied from 75-82% of the initial product. Table A summarizes the fraction yields for six different tragacanth samples. The values are based on single observations. It should be understood that yields will vary among the species depending on cultural conditions as well as process procedures. A commercial gum tragacanth ribbon product, Astragalus spp. #2 was converted to various sodium salt forms.

TABLE A

| | Tragacanth Fractions | | | |
|---|---|---|---|---|
| | Initial Product, g | Water Sol., g (%) | Water Insol., g (%) | Alcohol Sol., g (%) |
| A. parrowianus | 11.53 | 4.40 (38.7) | 4.28 (37.1) | 0.12 (1.0) |
| A. brachycentrus | 7.75 | 4.20 (54.2) | 1.90 (24.5) | 0.12 (3.4) |
| A. cerasocranus | 5.18 | 3.70 (71.4) | 0.50 (9.6) | 0.03 (0.6) |
| A. echidnaeformis | 18.59 | 12.60 (67.8) | 1.64 (8.8) | 0.69 (3.7) |
| A. echidnaeformis "elongata" | 10.42 | 7.10 (68.1) | 0.33 (3.2) | 0.40 (3.8) |
| Astragalus spp. #1 | 10.0 | 6.36 (63.6) | 1.02 (10.2) | 0.48 (4.8) |

The purified water-soluble fractions of tragacanth were characterized by acidity and viscosity of 1.0% solutions, infrared spectra and nitrogen analysis. Size exclusion chromatography (SEC) was also used for characterization. The physical characteristics serve to differentiate the water-soluble polysaccharides from each species. These physical parameters reported as single values are actually ranges that can vary depending on plant cultural conditions and process procedures, Table B.

Infrared spectroscopy (IR) was used to examine the water-soluble fractions. All of the naturally occurring polysaccharides contained absorption peaks due to carboxyl (COOH) at 1735 cm$^{-1}$ and carboxylate (COO$^-$) at 1610 cm$^{-1}$. The latter peak masked a weaker absorption at 1640 cm$^{-1}$, possibly amide. The IR values in Table B are a ratio of the integrated areas of the 1735/(1610+1640) peaks. These ratios vary and are an estimate of the relative amounts of these carboxy functional groups in the water-soluble fractions. A typical example of this section of the IR spectrum is shown in FIG. I for AV213. The carboxylate anion can be converted to free carboxyl by treatment with a cation exchanger in the hydrogen form such as Dowex, Amberlite, Bio-Rex, Aminex, Zeocarb, Lewatit, Wofatit, Rexyn, Kastel, Imac and other. All of the metal cations are removed and replaced by hydrogen. This unmasked the 1640 cm$^{-1}$ amide peak. In the case of AV213 the IR ratio represents COOH/CONH. IR spectroscopy is a method to monitor the interconversion of carboxylate salt and free carboxyl, and to measure the relative amounts of these functional groups in the purified products.

Using IR to monitor the products, a cation exchange process was used to convert all of the galacturonic acid carboxylate to carboxyl. This provided a polysaccharide different from the natural product that occurs in the gum exudate. The new product can be generated by batch or column cation exchange procedures, and is free of carboxylate anions and the corresponding metal cations components comprising that structure. Alcohol extraction removes all of the smaller metabolic compounds that occur in the gum exudate and also sterilizes the product. The monomolecular compounds are easily monitored using SEC, which separated these compounds from the polysaccharides.

TABLE B

Physical Characteristics of Water-Soluble Polysaccharides

| Name | Code | pH | Viscosity | IR ratio | N % |
|---|---|---|---|---|---|
| A. parrowianus | AV209 | 4.6 | 60 | 0.62 | 0.66 |
| A. brachycentrus | AV208 | 6.4 | 4430 | 0.71 | 0.45 |
| A. cerasocrenus | AV211 | 6.5 | 4170 | 0.81 | 0.16 |
| A. echidnaeformis | AV212 | 6.0 | 7260 | 0.74 | 0.60 |
| A. echidnaeformis "elongata" | AV210 | 5.7 | 8650 | 0.78 | 0.74 |
| Astragalus spp. #1 | AV213 | 2.6 | 124 | 1.96 | 0.28 |

The new product has good water solubility. It is free of metal cations and small molecular compounds. For the first time practical batch type purification processes have been devised to separate the immunomodulatory polysaccharides from other undesirable components in the crude gum exudates. These processes can be applied to the polysaccharide gum products from the Astragalus species reported here and also to related polysaccharides from *A. gossipinus, A. microcephalus, A. gummifer, A. kurdicus, A. adscendens, A. sherineh, A. elymaiticus, A. geminanus, A. globiflorus, A. myriacanthus, A. polixus, A. versus, A. sanganensis, A. brachycalyx, A. creticus, A. cylleneus, A. eriostylus, A. heratensis, A. leidocladus, A. pycnocladus, A. strobiliferus, A. stromatodes* and any other Tragacantha section, Astragalus species.

Polysaccharides were examined by size exclusion chromatography (SEC) on a Spherogel TSK 4000SW, 7.5×300 mm column. The eluant was pH 4.4 phosphate buffer:acetonitrile (9:1) delivered at 1.0 ml/minute. A UV detector was set at 210–220 nm and 0.01–0.1 AUF for 1.0% solutions of the polysaccharides. A typical chromatogram for a crude water-soluble extract fraction is shown in FIG. II. The polysaccharides are represented by the peaks in the 5 minute elution time zone. The peaks at 11.5 minutes and 15 minutes are due to the small molecules in the crude sample that are later extracted as alcohol-solubles. In FIG. III all of the undesirable small molecule impurities have been removed by alcohol extraction. SEC is a method that can thus be used to monitor the homogeneity of the polysaccharides. It also represents a method to identify polysaccharide mixtures from individual species by the differences in the polysaccharide peak pattern.

In a preferred process a solution of gum tragacanth Astragalus spp. #2 ribbon was converted to its free carboxyl form with an acidified cation exchange resin as in example 4. This resulted in a solution of pH 2.7. An infrared spectrum showed no carboxylate peak indicating complete exchange of all of the naturally occurring metal cations for hydrogen in the product. Small amounts of antimicrobial agents are added to maintain sterility, and these are later alcohol extracted. Portions of this solution were brought to pH 8.0–11.6 with sodium hydroxide. Infrared spectra indicate that at pH 8.0 neutralization is about 50%, with complete neutralization of the carboxyl COOH to carboxylate COO⁻ occurring only at pH 11.6. Several of these salt forms were isolated by freeze drying with alcohol extraction, or precipitation with alcohol to provide a series of five products. These sodium salt forms are more soluble and more stable in water than the naturally occurring metal cation salts which led to acidic solutions. The alcohol treatments serve to both sterilize the products and remove undesirable small molecules to provide polysaccharide-homogeneous products.

The carcinogen MNU (N-methyl-N-nitrosourea) administered to female rats induces the formation of mammary carcinomas. The water-soluble purified polysaccharides of tragacanth inhibited this tumor system in an 18 week study as shown in Table C. The polysaccharides were administered to the rats intraperitoneally in five doses at 1 day before MNU challenge, then 1, 2, 4 and 8 weeks afterward. At 63 days, one week after the last injection of polysaccharide, the effect on tumor incidence per rat for AV208 (*A. brachycentrus*) and AV212 (*A. echidnaeformis*) was significant at 4 and 3 total tumors respectively compared to 18 for controls. At 126 days, there was a significant reduction in the total number of tumors for each product. The most active product was AV208 where 14 surviving rats had 26 tumors total, or 1.73/rat. The 14 surviving control rats had 61 tumors total, or 4.07/rat. Multiplicity of tumors was definitely inhibited to varying degrees by treatment with the water-soluble purified polysaccharides of tragacanth. When the weekly data was plotted for the entire 18 weeks, charts indicated that continued treatment with polysaccharides beyond 8 weeks may have maintained the suppressive effects on tumor incidence. The similarity in results at 126 days for AV212 (*A. echidaneformis*) and AV210 (*A. echidnaeformis* "elongata") correlate with the taxonomic and chemotaxonomic similarities of these species. Body weight gain was not significantly affected in any of the treatment groups.

The amphotropic murine leukemia virus MuLV-10A1 has been isolated from wild mice trapped at several locations in Southern California. This retrovirus causes a splenic lymphoma in 95% or more of the rodents infected with it in the laboratory including NIH Swiss mice. The tumor develops as an enlarged spleen and is noticeable within 1–2 months. In our experiments, NIH Swiss mice were infected with this retrovirus two days after birth. The mice were given an intraperitoneal injection of polysaccharide on day 1, then ten more injections every other day for 21 days. Five water-soluble polysaccharides were administered, as well as a medium control (PBS) and a corn starch placebo. Results in Table D show that mean spleen weight in PBS controls and corn starch placebo were 147 mg and 160 mg respectively at 120 days. Normal NIH Swiss mice have a spleen weight of about 88 mg after this time. Therefore, virus-induced splenic lymphoma was initiated in the PBS controls, and corn starch had no inhibitory effects. In the water-soluble polysaccharide treated groups the mean spleen weight ranged from 105 mg for AV209 (*A. parrowianus*) to 123 mg for AV210 (*A. echidnaeformis* "elongata"). Average mean spleen weight for all twenty three tragacanth treated mice was 116 mg, or about a 50% inhibition. AV208 (*A. brachycentrus*) also performed well at 109 mg spleen weight. Results demonstrate that these tragacanth products have an inhibitory effect against the MuLV-10A1 induced splenic lymphomas.

TABLE C

Inhibition of MNU-Induced Mammary Tumors in Female Rats at 63 Days[a] and 126 Days

| | MNU Saline | MNU AV208[b] | MNU AV209[b] | MNU AV212[b] | MNU AV210[b] |
|---|---|---|---|---|---|
| Surviving rats[c] | 14 (15) | 14 (15) | 12 (15) | 11 (11) | 13 (13) |
| Total no. tumors | 61 (18) | 26 (4) | 47 (10) | 28 (3) | 30 (10) |
| Tumor incidence, % | 86.7 (60.0) | 73.3 (26.7) | 86.7 (53.3) | 81.8 (27.3) | 84.6 (61.5) |
| Tumors/rat | 4.07 | 1.73 | 3.13 | 2.55 | 2.31 |

TABLE C-continued

Inhibition of MNU-Induced Mammary Tumors in
Female Rats at 63 Days[a] and 126 Days

|  | MNU Saline | MNU AV208[b] | MNU AV209[b] | MNU AV212[b] | MNU AV210[b] |
|---|---|---|---|---|---|
|  | (1.20) | (0.27) | (0.67) | (0.27) | (0.77) |
| Weight gain, | 62.0 | 77.2 | 65.8 | 71.5 | 75.3 |
| % | (50.6) | (63.3) | (52.5) | (55.7) | (57.0) |

[a]Day 63 values in parenthesis
[b]Final of 5 injections of polysaccharide on day 56
[h]Initially 15 rats per group Tragacanth gum contains water-soluble and water-insoluble polysaccharides, protein, several metal ions and other small alcohol-soluble compounds. Results here confirm that a water-soluble fraction of tragacanth causes cancer inhibition. The anticancer effects of the water-soluble polysaccharides from individual Astragalus species varied as did their physical characteristics. The polysaccharide fractions from different species vary in their anticancer activity depending on the type of cancer and induction method. Evidence presented here indicates that there are structural differences among these Astragalus polysaccharides that will distinguish them as anticancer agents. For the first time, differences in immunomodulatory activity of tragacanth polysaccharides have been found to correspond to differences in physical characteristics of the products from different Astragalus species, Tragacantha section plants. In prior experiments commercial tragacanth gum was used. This commercial gum was composed of exudates from unidentified Astragalus plants supplied as ribbon or a ground powder. This disclosure contains a description of differences in anticancer activity among the various species specific tragacanth gum exudates.

TABLE D

Inhibition of Virus-Induced Splenic Lymphoma in Mice at 120 Days

| Polysaccharide + MuLV-10A1 | No. mice[a] | Splene wt., mg mean ± s.d. |
|---|---|---|
| PBS controls | 6 | 147 ± 35 |
| conrstarch controls | 6 | 160 ± 43 |
| AV208 | 2 | 109 ± 3 |
| AV209 | 5 | 105 ± 9 |
| AV210 | 3 | 123 ± 5 |
| AV211 | 4 | 115 ± 10 |
| AV212 | 9 | 122 ± 12 |

[a]Newborn male and female

Three of the tragacanth polysaccharide products AV208, AV212 and AV213 were tested for activity vs. a lethal Punta toro virus in mice. Single intraperitoneal administration dose levels were 12.5–200 mg/kg for the three products, then 0.78–50 mg/kg for AV208. The products were found to be active when administered 24 hrs pre, 4 hrs post and 24 hrs post virus infection, with post treatment at lower doses most effective. Experiment duration was 21 days, Tables E and F.

The data in these tables show that AV208 elicits a 100% survival rate among 10 mice after a single 24 hour post dose of 6.25 mg/kg. At 1.56 mg/kg 9/10 mice survived. AV208 is more active at lower doses of 1–6 mg/kg than at 100–200 mg/kg doses. There was no noticeable toxicity for these three products up to 200 mg/kg, and they were all more active than ribavirin, an established antiviral drug. The mean liver titre and mean serum virus titre for mice treated with ribavirin at 350 mg/kg were 1.6 and 4.3 respectively, compared to AV208 treated mice at 6.25 mg/kg which were 0.3 and 0.4. Furthermore, AV208 has little effect on the liver enzymes serum glutamic oxalic transaminase (SGOT) and serum glutamic pyruvic transaminase (SGPT) compared to ribavirin which inhibits these enzymes. AV212 has antiviral activity comparable to AV208. These tragacanth polysaccharide products stimulate the immune system at low doses while apparently suppressing it at higher doses, a characteristic of some immunomodulatory agents. These antiviral results indicate that these same polysaccharides tested vs the MuLV-10A1 induced splenic lymphoma in mice enhanced immunomodulatory activity against the antigenic retrovirus as well as the antigenic cancer cells.

This is the first time that autochthonous cancers and viruses have been inhibited by tragacanth preparations. It is the first time that cancers in the mammary gland and in the spleen have been inhibited, both of which represent malignant tumors away from the site of injection of polysaccharide. It is the first time that chemical and virus induced tumors have been inhibited. Hitherto, only transplanted suspended ascites cancer cells cultured in the peritoneal cavity have been inhibited from multiplying by tragacanth, also injected into the peritoneal cavity. Results reported here indicate for the first time that water-soluble tragacanth polysaccharides can be used to inhibit cancer away from the peritoneal cavity and prevent virus replication. Because of the intraperitoneal administration dose protocols, it is apparent that the water-soluble polysaccharides act by an immunomodulatory mechanism involving macrophage, the peritoneum being rich in macrophage. Polysaccharides are not absorbed from the gastrointestinal system, and they are not know to be absorbed into the circulation unaided from the peritoneal cavity. These results are new, unique and useful for the treatment of cancer, viral and other diseases where there is an immunodeficiency.

TABLE E

Effect on Punta Toro Virus[a] Infections in Mice[b]

| Code | Dosage 24 hr post mg/kg[c] | Toxic Controls Surv./ Total | Toxic Controls Host wt. Change, g[d] | Infected-Treated Surv./ Total | Infected-Treated MST[e] days |
|---|---|---|---|---|---|
| AV208 | 200 | 5/5 | −0.7 | 0/10 | 5.0 |
|  | 100 | 5/5 | −0.7 | 8/10** | 5.0 |
|  | 50 | 5/5 | −0.3 | 7/10** | 5.7 |
|  | 25 | 5/5 | −0.3 | 10/10** | >21.0** |
|  | 12.5 | 5/5 | −0.1 | 10/10** | >21.0** |
| Ribavirin | 350 | 5/5 | 0.4 | 9/10** | 7.0 |
| Saline | — | — | — | 4/20 | 4.8 |
| Normals | — | 5/5 | 0.1 | — | — |
| AV212 | 200 | 5/5 | — | 10/10** | >21.0** |
|  | 100 | 5/5 | — | 10/10** | >21.0** |
|  | 50 | 5/5 | — | 2/10 | 10.6** |
|  | 25 | 5/5 | — | 10/10** | >21.0** |
|  | 12.5 | 5/5 | — | 9/10** | 17.0 |
| Ribavirin | 350 | 5/5 | — | 10/10** | >21.0** |
| Saline | — | — | — | 8/20 | 5.2 |
| Normals | — | 5/5 | — | — | — |
| AV213 | 200 | 5/5 | 0.1 | 5/10* | 6.4 |
|  | 100 | 5/5 | 0.1 | 8/10** | 5.5 |
|  | 50 | 5/5 | 0.0 | 5/10* | 5.0 |
|  | 25 | 5/5 | −0.2 | 10/10** | >21.0** |
|  | 12.5 | 5/5 | −0.3 | 4/10 | 5.8** |
| Ribavirin | 350 | 5/5 | 0.2 | 8/10** | 8.5 |
| Saline | — | — | — | 2/20 | 4.4 |

TABLE E-continued

Effect on Punta Toro Virus[a] Infections in Mice[b]

| Code | Dosage 24 hr post mg/kg[c] | Toxic Controls Surv./ Total | Toxic Controls Host wt. Change, g[d] | Infected-Treated Surv./ Total | Infected-Treated MST[e] days |
|---|---|---|---|---|---|
| Normals | — | 5/5 | 0.5 | — | — |

[a]Adames strain Punta toro virus injected s.c.
[b]11.3–15.0 g (3–4 wk) C57BL/6 mice
[c]Single dose in sterile saline injected i.p. 24 hrs post virus infection
[d]Difference between initial weight at start of treatment and weight eighteen hours following final treatment of toxicity control mice.
[e]Mean survival time of mice dying on or before day 21.
*P <0.05
**P <0.01

TABLE F

Effect on Punta Toro Virus and Liver Toxicity in Mice

| Compound | Dosage (mg/kg/day) | Toxicity controls Surv/ Total | Toxicity controls Host Wt. Change[a] (g) | Infected Treated Surv/ Total | Infected Treated MST[b] (days) | Infected Treated Mean Liver Score[c] | Infected Treated SGOT Neg./ Total[d] (Mean) | Infected Treated SGPT Neg./ Total[e] (Mean) | Infected Treated Mean Liver Virus Titer[f] ($log_{10}$) | Infected Treated Mean Serum Virus Titer[f] ($log_{10}$) |
|---|---|---|---|---|---|---|---|---|---|---|
| AV208 | 50 | 5/5 | −1.2 | 10/10** | >21.0** | 0.4** | 10/10**(106**) | 10/10**(32**) | 0.0** | 0.2** |
|  | 25 | 5/5 | −0.8 | 10/10** | >21.0** | 1.0** | 7/10**(233**) | 8/10**(91**) | 1.2** | 0.3** |
|  | 12.5 | 5/5 | −0.2 | 10/10** | >21.0** | 0.8** | 6/10**(271**) | 6/10**(139**) | 0.5** | 0.2** |
|  | 8.25 | 5/5 | −0.3 | 10/10** | >21.0** | 1.1** | 1/10(384**) | 1/10(291**) | 0.3** | 0.4** |
|  | 3.13 | 5/5 | 0.3 | 9/10** | 4.0 | 0.9** | 0/10(797**) | 0/10(1002**) | 0.3** | 0.7** |
|  | 1.56 | 5/5 | 0.3 | 9/10** | 4.0 | 0.5** | 0/10(1666) | 0/10(1569**) | 1.4** | 1.9** |
|  | 0.78 | 5/5 | 0.2 | 7/10 | 5.3 | 1.2** | 1/10(1775**) | 0/10(2929**) | 2.4** | 3.0** |
| Ribavirin | 350 | 5/5 | 0.0 | 10/10** | >21.0** | 0.5** | 8/10**(165**) | 9/10**(79**) | 1.6** | 4.3 |
| Saline | — | — | — | 7/20 | 5.2 | 3.1 | 0/20(7571) | 0/20(7772) | 5.1 | 4.8 |
| Normals | — | 5/5 | 0.4 | — | — | 0.0 | 5/5(94) | 5/5(22) | 0.0 | 0.0 |

[a]Difference between initial weight at start of treatment and weight 18 hr following final treatment of toxicity control mice.
[b]Mean survival time of mice dying on or before day 21.
[c]Scores of 0 (normal liver) to 4 (maximal discoloration) assigned to each liver removed on day 4 (animals dying prior to day 4 assigned a liver score of 4).
[d]Serum glutamic oxalic transaminase levels of <200 Sigma-Fraenkel units/ml.
[e]Serum glutamic pyruvic transaminase levels of <100 Sigma-Fraenkel units/ml.
[f]Geometric mean.
*P <0.05
**P <0.01

EXAMPLES

EXAMPLE 1

Polysaccharide Fraction Purification From *A. parrowianus*

*A. parrowianus* tragacanth ribbons, 11.53 grams, were stirred in 200 ml of methanol for several hours. The ribbons were collected and air dried weighing 11.00 grams. The dried ribbons were then suspended in 1100 ml of distilled water and stirred overnight at ambient temperature in a stoppered three liter round bottom flask. The resulting opaque suspension was centrifuged at 2400 rpm for at least 60 minutes. A supernatant solution of water-soluble polysaccharides was decanted from the gel and heavier nugget. This less soluble gel and nugget fraction was mixed well with additional distilled water and again centrifuged. The supernatant solution was decanted from the insolubles, combining with the water-soluble first extraction.

The water-soluble fraction was freeze dried, resulting in a white cotton-like product. This was mulled in about 400 ml of methanol to remove alcohol-solubles and to further sterilize the product. There was always a small quantity of residual water in these freeze dried products, which was also extracted by the methanol leaving an essentially anhydrous polysaccharide. Filtration and air drying provided 4.40 grams (38.7%) of a white, fibrous, matted, water-soluble product. Each of the other water-soluble polysaccharide fractions were similar in appearance.

The less soluble gel and nugget fraction was treated with ethanol to completely precipitate the fraction termed water-insolubles. The suspension was centrifuged and the ethanol supernatant was decanted. The water-insoluble nugget was air dried and crushed to a white powder, 4.28 g (37.1%). Alcohol extractions and washes were combined and evaporated to dryness on a rotary evaporator under vacuum. In the case of *A. parrowianus* only 0.12 grams of alcohol-solubles were recovered.

A 1% solution of each of the water-soluble polysaccharide fractions, AV208-AV213, from the five species and commercial product was prepared. The acidity of these solutions was measured with a pH meter. The viscosity of the same 1% solutions was measured with a Brookfield viscometer at ambient temperature of about 21° C. Infrared spectra of the water-soluble fractions were taken with a Pye Unicam SP3-200 spectrophotometer interfaced with an electronic data processor. Samples were prepared as films by evaporation of the 1% solutions on silver bromide plates under a heat lamp. The products each showed two carbonyl absorption peaks, one at 1735 cm$^{-1}$ due to free-carboxyl (COOH) and a second peak at 1610 cm$^{-1}$ due principally to carboxylate (COO−), plus a masked 1640 cm$^{-1}$ peak probably due to amide (CONH). The peak areas were integrated and the ratios were calculated. Nitrogen analyses were an indication of the protein content of the polysaccharides. An estimate of protein is obtained by multiplying the nitrogen analysis by 6.3. Table B summarized these physical characteristics.

EXAMPLE 2

Polysaccharide Fraction Purification From *A. brachycentrus*

*A. brachycentrus* tragacanth ribbons, 7.75 grams, were suspended in 800 ml of distilled water in a three liter flask equipped with a mechanical stirrer. After stirring for 12 hours at ambient temperature the suspension was centrifuged for 60 minutes at 2400 rpm. The supernatant solution of water-soluble polysaccharides was decanted from the gel and insoluble nugget. The less soluble residues were washed by mulling in 200 ml of distilled water, then centrifuged again. The supernatant water extracts were combined and freeze dried at −54° and 20–40 mt. The white cotton-like product was mulled in methanol to extract the alcohol-solubles. The product was collected on a sintered glass filter funnel and dried overnight in a vacuum dessicator. The dry water-soluble product weighed 4.20 grams (54.2%). The gel and insolubles were mulled in ethanol to precipitate an insoluble fraction. The total insolubles were collected on a filter, washed with ethanol and air dried to a white powder weighing 1.90 grams (24.5%). The combined alcohol extracts were stripped to dryness in a rotary evaporator with vacuum, weighing 0.26 grams (3.4%).

EXAMPLE 3

Polysaccharide Fraction Purification From Astragalus spp. #1

A commercial tragacanth powder, 10 grams, termed Astragalus spp. #1 was suspended in 800 ml of distilled water containing 20 drops of Zephiran, a 0.13% solution of benzalkonium chloride, as an antimicrobial agent. The stoppered system was stirred at a moderate rate to disperse and dissolve the powder, which took several hours. When all of the powder had dispersed or dissolved, Dowex 50W×8 cation exchange resin in the hydrogen form was added and the batch was stirred well. Infrared spectra were taken on samples before and after treatment with the cation exchange resin. After the treatment a 1610 cm$^{-1}$ peak due to carboxylate had converted to carboxyl at 1735 cm$^{-1}$, and an amide peak at 1640 cm$^{-1}$ was unmasked. Before treatment the IR ratio of 1735/1610 peaks was 0.80. After treatment the IR ratio of 1735/1640 peaks was 1.96. Treatment with additional Dowex 50W×8 resin in the batch and on a column had no further effect on the carboxyl and amide peaks, FIG. I.

The mixture was centrifuged at 2600 rpm for an hour separating the components into three phases consisting in an upper relatively transparent phase, a middle gel, and a lower resin. The upper water-soluble fraction was carefully decanted from the gel plus resin. The lower level phases were further extracted with 200 ml of distilled water and again centrifuged. The upper layer was combined with the original water-soluble fraction. After freeze drying the water-solubles at −54° C. and 10–20 mt, a white cotton-like mass resulted. This was suspended in 300 ml of methyl alcohol and stirred overnight to extract the alcohol-solubles. SEC curves taken before and after the methyl alcohol extraction demonstrated that this procedure completely removed the alcohol-solubles which appeared as an elution peak in the 11.5 minute range, FIG. II and III. The water-soluble fraction worked up in this manner provided a white cotton-like fibrous mass, collected on a sintered glass filter and dried in a vacuum dessicator, 6.36 grams (63.6%). The insoluble gel fraction was freeze dried and the alcohol-soluble fraction was processed as in the prior examples. The alcohol-solubles consisting of small molecular compounds are much more strongly absorbing at at 210–222 nm, than are the polysaccharides.

EXAMPLE 4

Polysaccharide Acid and Salt Forms From Astragalus spp. #2

Thirty three grams of a commercial tragacanth ribbon, Astragalus spp. #2, were treated with 300 ml methanol with stirring for several hours. The ribbon product was collected and air dried protecting it against microbial contamination. The resulting 32 grams of sterilized-extracted ribbon was suspended in 3000 ml of distilled water containing 32 mg of benzalkonium chloride (Zephiran). After four hours of stirring the ribbon had dissolved, giving a highly viscous solution of pH 4.7. Sixty grams of Dowex 50W×8 cation exchange resin was then added to the batch with continued stirring. Within twenty minutes the acidity had dropped to pH 2.7. An infrared spectrum indicated that all of the carboxylate absorption at 1610 cm$^{-1}$ had converted to carboxyl at 1735 cm$^{-1}$, with a small amount of carboxamide at 1640 cm$^{-1}$. The mixture was centrifuged at 2600 rpm for an hour separating the ion exchange resin and a small amount of insolubles and gel from the clear colorless supernatant. Several products with varying acid and sodium salt contents were prepared from this supernatant solution.

Freeze Dried Product pH 2.7

A portion of the supernatant solution was freeze dried, then extracted with methanol for six hours with good stirring to provide a white, fibrous, matted carboxylic acid polysaccharide product, pH 2.7. It was dried under vacuum in a desicator to 1.54 grams.

Freeze Dried Product pH 8.0

The remaining supernatant solution was brought to pH 8.0 by the dropwise addition of 1N sodium hydroxide solution with good stirring, using a pH meter to monitor acidity. The pH adjusts slowly to the added alkali due to the high viscosity of the solution. A major portion was freeze dried and extracted with methanol as above to remove alcohol-solubles and maintain sterility. The resulting white, fibrous, matted polysaccharide, pH 8.0, was dried in a dessicator under vacuum to yield 18.1 grams of product. An infrared spectrum indicated this product is about 40% in the carboxylic acid form and 60% in the carboxylate sodium salt form.

Precipitated Product pH 8.0

A portion of the pH 8.0 solution was added with good mechanical stirring to three volumes of isopropyl alcohol over a period of about one hour. A stringy mass of product collected around the stirrer blade and shaft. The white matted cotton-like product was collected on a non-cellulosic filter disc. After washing with methanol and drying the product weighed 4.30 grams. A trace amount of small molecular impurities was removed by extraction of the mass for several hours in ethanol with good stirring. The resulting product was polysaccharide-homogeneous by SEC and weighed 4.26 grams. Elution time for the polysaccharide was 4.6 minutes, with a shoulder on this peak at 5 minutes, and no small molecule peaks in the 11–12 minute elution time zone.

Precipitated Product pH 9.0

A portion of the pH 8.0 solution was brought to pH 9.0 with the careful dropwise addition of 1N sodium hydroxide. The product was precipitated by slowly adding the solution to three volumes of ethanol with good stirring. The stringy white product was collected on a non-cellulosic filter disc, washed well with ethanol and dried to 4.33 grams. An infrared spectrum indicated there was only a small increase in the sodium salt form compared to the pH 8.0 product.

Precipitated product pH 11.6

The remainder of the pH 8.0 solution was treated with 1N sodium hydroxide and infrared spectra were used to monitor conversion of carboxylic acid to the neutralized sodium carboxylate salt form. This conversion was only about 80% complete at pH 10.7, and 95% complete at pH 11.4. At pH 11.6 the carboxylic acid was completely converted to its sodium salt form. The product was precipitated by addition to ethanol providing 2.19 grams of a dry, white fibrous, matted product similar in appearance to all of the other tragacanth derived polysaccharide products reported herein.

EXAMPLE 5

Small Molecular Non-Polysaccharide Impurities

The alcohol-soluble extracts of the five identified species were examined by thin layer chromatography (TLC) on silica gel G plates, and by high performance liquid chromatography (HPLC) on 5 micron silica columns. By TLC each extract was found to contain as many as four different small molecular compounds using several detection methods including 10% sulfuric acid spray with heat. There were at least seven different distinct compounds detected by TLC in the five alcohol extracts, plus origin material. HPLC with ultraviolet detection indicated the presence of at least six UV absorbing compounds, none of which corresponded to another five or more compounds detected with a refractive index detector. These chromatographic analyses indicate there are probably fifteen or more distinct small molecular compounds in the tragacanth gum exudates, none of which appear to be reducing monosaccharides. These impurities constitute up to 5% of the total gum exudate, and have been implicated as the cause of negative side effects exhibited by the whole gums.

EXAMPLE 6

Inhibition Of Chemical-Induced Tumor in Rats

The carcinogen N-methyl-N-nitrosourea (MNU) was administered to 50 day old Sprague-Dawley female rats in a single intravenous dose of 50 mg/kg in acidified saline. These rats were separated into test groups of 15 animals per test. One group of controls received MNU in saline, and a second group received saline alone. Twenty four hours prior to MNU injection the treatment rats were administered an initial intraperitoneal injection of a 1.0% water-soluble polysaccharide in saline at 100 mg/kg. Doses of polysaccharides at 100 mg/kg i.p. were repeated at 1, 2, 4 and 8 weeks. Rats were weighed and checked by palpation weekly, then terminated at 126 days by carbon dioxide asphixiation. Mammary glands were removed and the tumors counted. No tumors were noted in the control animals receiving saline alone. Results are in Table C.

EXAMPLE 7

Inhibition of Virus-Induced Tumor in Mice

Newborn NIH Swiss mice were injected with 1,000,000 focus forming units (0.02 ml) of wild mouse retrovirus (MuLV-10A1) intraperitoneally, two days after birth. The water soluble polysaccharides including a corn starch placebo were dissolved in phosphate buffered saline (PBS) at 0.5% concentrations. The polysaccharide solutions were administered intraperitoneally on days 1, 3, 5, 7 and 9 at 0.02 ml; on days, 11, 13 and 15 at 0.05 ml; and, on days 17, 19 and 21 at 0.08 ml. Controls received PBS solutions following the initial dose of MuLV. All animals were maintained with ad lib laboratory chow. Each group of animals was kept with their mother until day 28, when they were separated with respect to sex. At 120 days of age the animals were sacrificed, spleens were removed and weighed. Increased spleen weight is directly related to progression of the tumor. The average spleen weights in the treated mice were less than the PBS and corn starch placebo controls. Results are in Table D.

EXAMPLE 8

Treatment of Virus Infection in Mice

A lethal Adames strain Punta toro virus was injected subcutaneously into 3 week old C57BL/6 mice. Twenty four hours post infection the mice were treated with the polysaccharides in sterile saline at 0.78–200 mg/kg intraperitoneally. At each dose level 10 mice were infected and treated with 5 mice receiving the polysaccharide alone as toxic controls. Additional controls included infected + ribavirin (350 mg/kg) treated mice, infected + saline only treated mice, and normals. Duration of the experiment was 21 days. The antiviral activity and toxicity were monitored by mean survival time (MST), liver discoloration, serum and liver virus titres, liver levels of the enzymes SGOT and SGPT, and weight change in the toxicity control mice 18 hours post treatment. Results are in Table E for higher doses of AV208, AV212 and AV213, and in Table F for lower doses of AV208. For AV208 significant activity was seen at six doses from 1.56–50 mg/kg.

REFERENCES CITED

1. Anderson, D. M. W., Evidence for the Safety of Gum Tragacanth (Asiatic Astragalus spp.) and Modern Criteria for the Evaluation of Food Additives, Food Addit. Contam., 6:1(1989).

2. Anderson, D. M. W. and M. M. E. Bridgeman, The Composition of Proteinaceous Polysaccharides Exuded by Astragalus Microcephalus, *A. Gummifer* and *A. Kurdicus*—Sources of Turkish Gum Tragacanth, Phytochem. 24:2301(1985).

3. Anderson, D. M. W. and D. A. D. Grant, Chemical Composition of the Nitrogen Containing Gum Tragacanth Exudates From Asiatic Astragalus Species Grown in North America, Food Hydrocolloids, 3:217(1989).

4. Bachman, E., E. Weber, M. Post and G. Zbinden, Biochemical Effects of Gum Arabic, Gum Tragacanth, Methylcellulose and Carboxymethylcellulose-Na in Rat Heart and Liver, Pharmacol., 17:39(1978).

5. Carr, I and E. M. F. Roe, The Change in Shape of Peritoneal Macrophages after Stimulation as Studied by the Tragacanth-PAS Technique, J. Roy Microscop. Soc., 88:205(1967).

6. Galbraith, W., F. Mayhew and E. M. F. Roe, Mode of Inhibitory Action of Tragacanth Powder on the Growth of the Landschutz Ascites Tumor, Brit. J. Cancer, 16:163(1962).

7. Galbraith, W., F. Mayhew, J. Sugar and E. M. F. Roe, Physical Changes Measured by Interference Microscopy in Fresh Landschutz Ascites Tumor Cells After Tragacanth and Mannitol Mustard Treatments, Brit. J. Cancer, 17:738(1963).

8. Informatics, Inc., GRAS (Generally Recognized As Safe) Food Ingredients: Gum Tragacanth, Report PB-221-204, publ. National Technical Information Services, July 1972.

9. Mayhew, E. and E. M. F. Roe, Changes in the Mitotic Index of the Landschutz Ascites Tumor After Treatment With Tumor-Inhibitory or Non-Inhibitory Samples of Gum Tragacanth or Gum Karaya, Brit. J. Cancer, 18:528(1964).

10. Mayhew, E. and E. M. F. Roe, Changes in the Permeability of Landschutz Ascites Tumor Cells to Vital Stains After Treatment With Tumor-Inhibitory or Modified Samples of Gum Tragacanth or With Gum Karaya, Brit. J. Cancer, 18:537(1964).

11. Mayhew, E. and E. M. F. Roe, Microscopical Observations of the Effects of Tumor-Inhibitory and Non-Inhibitory Samples of Gum Tragacanth on Landschutz Ascites Tumor Cells, J. Roy Microscop. Soc., 84:235(1965).

12. Nakahara, W., F. Fukuoka, Y. Maeda and K. Aoki, Host Mediated Anitumor Effects of Some Plant Polysaccharides, Gann. 55:283(1964).

13. Osswald, H., Der Einfluss verschiedener Polysaccharide auf das Wachstumsverhalten des Ehrlich-Ascites Tumors, Arzneim.-Forsch., 18:1495(1968).

14. Roe, E. M. F., Growth Inhibition of Mouse Ascites Tumor Cells by Powdered Tragacanth (Tragacanthae Pulvis, B. P.), Nature, 184:1891(1959).

15. Roe, E. M. F., H. Smyth and E. Flahavan, Action of Tumor-inhibitory Gum Tragacanth on Potassium Permeability of Ascites Tumor Cells and Partial Characterization of the Cytotoxic Component, Cancer Res., 32:2067(1972).

16. Seljelid, R., J. Bogwald and A. Lundwall, Glycan Stimulation of Macrophages in Vitro, Exp. Cell. Res., 131:121(1981).

17. Wilson, R. O., Process for the Purification of Natural Gums, U.S. Pat. No. 3,226,378(Dec. 28, 1965).

18. Wood, W. H., Manufacture of Acids and Salts from Gums, U.S. Pat. No. 2,666,759(Jan. 19, 1954).

What is claimed is:

1. A process for separating, purifying and modifying the polysaccharide fractions of gum tragacanth from Astragalus species plants comprising:
    a) Extracting with water to separate water-insolubles from the desired water-soluble fraction;
    b) Removing the naturally occurring cations from the water-soluble fraction with an ion exchange resin;
    c) Adjusting the pH to between 2.5 and 12 with an alkali metal base;
    d) Recovering the polysaccharide product by freeze drying, spray drying, rotary vacuum evaporation, or precipitation with a lower alcohol selected from the group of methanol, ethanol, propanol and isopropanol; and
    e) Extracting the said polysaccharide product with a lower alcohol selected from the group of methanol, ethanol, propanol and isopropanol in order to both sterilize the product and to remove residual small molecular weight impurities.

2. The polysaccharide product prepared by the process of claim 1.

3. The product of claim 2 wherein the polysaccharide fraction is obtained from *Astragalus parrowianus*.

4. The product of claim 2 wherein the polysaccharide fraction is obtained from *Astragalus brachycentrus*.

5. The product of claim 2 wherein the polysaccharide fraction is obtained from *Astragalus cerasocrenus*.

6. The product of claim 2 wherein the polysaccharide fraction is obtained from *Astragalus echidnaeformis*.

7. The product of claim 2 wherein the polysaccharide fraction is obtained from *Astragalus echidnaeformis'-'elongata*".

8. The product of claim 2 wherein the polysaccharide fraction is obtained from commercial gum tragacanth.

9. The product of claim 2 wherein the polysaccharide is obtained from an Astragalus species tragacanth section plant.

* * * * *